(12) United States Patent
Son et al.

(10) Patent No.: US 6,953,947 B2
(45) Date of Patent: Oct. 11, 2005

(54) ORGANIC THIN FILM TRANSISTOR

(75) Inventors: Se-Hwan Son, Yuseong-gu (KR);
Seokhee Yoon, Yuseong-gu (KR);
Hyeon Choi, Yuseong-gu (KR);
Changhee Lee, Yeonsoo-gu (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 10/781,076

(22) Filed: Feb. 17, 2004

(65) Prior Publication Data

US 2004/0164294 A1 Aug. 26, 2004

Related U.S. Application Data

(63) Continuation-in-part of application No. 09/914,731, filed on Aug. 30, 2001, now Pat. No. 6,720,573.

(30) Foreign Application Priority Data

Dec. 31, 1999 (KR) .................................. 1999-067746
Dec. 26, 2000 (KR) .................................. 2000-82085

(51) Int. Cl.$^7$ .......................... H01L 35/24; H01L 51/00
(52) U.S. Cl. .................................. 257/40; 257/40
(58) Field of Search .................. 257/40, E51.005, 257/E51.027

(56) References Cited

U.S. PATENT DOCUMENTS

| | | | | |
|---|---|---|---|---|
| 4,780,536 A | * | 10/1988 | Czarnik et al. | 544/225 |
| 5,796,121 A | * | 8/1998 | Gates | 257/59 |
| 6,720,573 B2 | * | 4/2004 | Son et al. | 257/40 |

OTHER PUBLICATIONS

ABSTRACT—"Contact dependent of a–sexithienyl thin–film transistor characteristics"; Authors: Lin, Y.Y., Gundiach, D.J., Jackson, T.N., Materials Research Society Symposium Proceedings; 1996.

ABSTRACT—"Screen printed organic thin film transistor (OTFTs) on a flexible substrate"; Authors: Caprice Gray, Jianna Wang, Gregg Duthaler, Andrew Ritenour and Paul S. Drzale; The International Society for Optical Engineering (SPIE); 2003.

"Organic electronics: Introduction"; Authors: J.M. Shaw and P.F. Seidler; International Business Machines Corp. (IBM) J. Res. & Dev., vol. 45, No. 1; Jan. 2001; pp. 3–9.

"Printing Process Suitable for Reel–to–Reel Production of High–Performance Organic Transistors and Circuits"; Authors: John A. Rogers, Zhenan Bao, Anita Makhija and Paul Braun; WILEY–VCH Verlag GmbH & Co.; Advanced Materials, vol. 11, No. 9, 1999; pp. 741–745.

(Continued)

Primary Examiner—Tom Thomas
Assistant Examiner—Joseph Nguyen
(74) Attorney, Agent, or Firm—Cantor Colburn LLP

(57) ABSTRACT

An organic transistor including an organic layer is provided. The organic layer includes at least one compound represented by the Chemical Formula I.

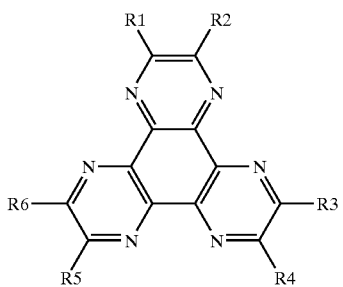

Formula I

19 Claims, 6 Drawing Sheets

OTHER PUBLICATIONS

"Synthetic Chemistry for Ultrapure, Processable, and High-Mobility Organic Transistor Semiconductors"; Authors: Howard E. Katz, Zhenan Bao and Sylvain L Gilat; American Chemical Society; Accounts fo Chemical Research, vol. 34, No. 5; 2001; pp. 359-369.

"Building Blocks for n-Type Organic Electronics: Regiochemically Modulated Inversion of Majority Carrier Sign in Perfluoroarene-Modified Polythiophene Semiconductors"; Authors: Antonio Facchetti, Myung-Han Yoon, Charlotte L. Stern, Howard E. Katz and Tobin J. Marks; Communications; WILEY-VCH Verlag GmbH & Co.; Angew. Chem. Int. Ed., vol. 42; 2003; pp. 3900-3903.

"The Physical hemistry of Organic Field-Effect Transistors"; Authors: H.E. Katz and Z. Bao; Feature Article; American Chemical Society; J. Phys. Chem. B, vol. 104, No. 4, 2000; pp. 671-678.

"New Air-Stable n-Channel Organic Thin Film Transistors"; Authors: Zhenan Bao, Andrew J. Lovinger and Janelle Brown; American Chemical Society; J. Am. Chem. Soc., vol. 120, No. 1; 1998; pp. 207-208.

* cited by examiner

ORGANIC THIN FILM TRANSISTOR

CROSS REFERENCE TO RELATED APPLICATIONS

This application is a continuation-in-part claiming priority to U.S. patent application Ser. No. 09/914,731, filed Aug. 30, 2001, now U.S. Pat. No. 6,720,573, PCT filed on Dec. 27, 2000, which is based on application No. 10-1999-067746 and No. 10-2000-82085 filed in the Korean Industrial Property Office on Dec. 31, 1999 and Dec. 26, 2000, respectively, the content of which is incorporated hereinto by reference.

BACKGROUND OF THE INVENTION

1. Field of the Invention

The present invention relates to new organic materials used in organic transistors. More particularly, the present invention pertains to novel organic compounds facilitating the ohmic contact between semi-conducting layer and electrodes and use in organic thin film transistors.

2. Description of the Related Art

Thin film field-effect transistors (FETs) comprise the basic building blocks for microelectronics. A FET has three electrodes (e.g., source, drain, and gate electrodes), an insulator layer, and a semiconductor layer. A FET operates as a capacitor where a semiconductor layer is a conducting channel between two electrodes, i.e., the source and the drain. The density of charge carriers in the channel is modulated by voltage applied to the gate electrode, so that the electric charge flow between the source and the drain electrodes can be controlled by voltage applied to the gate electrode.

There has been great interest recently in the development of FETs using organic semi-conducting materials. With organic semi-conducting materials in FETs, electronic devices can be manufactured in a printing method, such as screen-printing, ink-jet printing, and/or micro-contact printing. In addition, these materials can be processed at a much lower substrate temperature and with little or no vacuum involved, as compared to the typical inorganic semi-conducting materials. Therefore, electronic devices, including FETs, that use organic semi-conducting materials can be flexible and less costly to produce compared with using inorganic semi-conducting materials.

Different types of organic materials such as small molecule, polymers and oligomers have been tested as organic semi-conducting materials in FETs since the 1980s. With concerted effort in this area, the performance of an organic FET has improved from $10^{-5}$ cm$^2$/V s to 1 cm$^2$/V s in terms of charge carrier mobility in a FET (J. M. Shaw, P. F. Seidler, IBM J. Res. & Dev., Vol. 45, 3 (2001)). The performance of an organic transistor is now comparable to that of an amorphous silicon transistor, so that organic transistors can be applied to E-paper, smart cards, and possibly displays.

Important electronic devices, which can be manufactured with semi-conducting organic materials, include organic light emitting diodes, organic solar cells, and organic transistors. In these devices, the electrical contact between the semi-conducting organic materials and electrodes is crucial to improving the performance of these devices. For example, the charge-carrier injection layers, such as hole-injection and electron-injection layers, are interposed between semi-conducting layers and electrodes to improve the performance of organic light emitting diodes. Even though the operation mode of the organic transistor is different from that of the organic light emitting diode, electrical contact between the semi-conducting layer and source and drain electrodes has a profound effect upon the performance of the organic transistor. It has been reported that the performance of the organic transistor depends upon the materials of choice for the source/drain contact metal (Y. Y. Lin et al. Materials Research Society Symposium Proceedings (1996), 413(Electrical, Optical, and Magnetic Properties of Organic Solid State Materials III), 413–418. CODEN: MRSPDH ISSN: 0272-9172). In this report, the metals with high work function (Pd, Pt, and Au) showed the best performance while the metal (Al) with relatively low work function showed a significantly degraded performance. Therefore, metals with high work function such as gold have been used for the source/drain electrode materials in most organic transistors. However, high work metals, which are novel metals, are expensive and hard to process using industrial methods, thus restricting their application and structure in organic transistors.

SUMMARY OF THE INVENTION

The present invention provides an organic transistor comprising organic compounds that can facilitate the ohmic contact between a semi-conducting layer and electrodes and improve the performance of organic transistor by forming a stable interface between a semi-conducting layer and source/drain electrodes.

The present invention further provides an organic transistor with various conducting materials as source/drain electrodes by introducing an organic layer between semi-conducting materials and source/drain electrodes.

The present invention further provides an organic transistor including an organic layer having at least one compound represented by Chemical Formula I.

Formula I

The present invention further provides an organic transistor, comprising an organic layer inserted between a semi-conducting layer and a source or drain electrode, wherein the organic layer includes at least one compound represented by the Chemical Formula I.

The present invention further provides a method for manufacturing an organic transistor which comprises inserting an organic layer between a semi-conducting layer and source or drain electrode to improve the electrical contact between the semi-conducting layer and the source or drain electrode, wherein the organic layer includes at least one compound represented by the Chemical Formula I.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

Reference numeral 11 indicates a drain electrode, 12 an insulator layer, 13 a substrate, 14 a semi-conducting layer, 15 a source electrode, 16 a gate electrode, 17 an organic layer. W and L in FIG. 5 correspond to an organic transistor channel width and length, respectively.

DETAILED DESCRIPTION OF THE INVENTION

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, the drawings and description are to be regarded as illustrative in nature, and not restrictive.

The present invention provides an organic transistor in which an organic layer comprising at least one compound represented by the following Chemical Formula I is disposed between a semi-conducting layer and source/drain electrodes:

Formula I

In Formula I, R1–R6 are independently chosen from the group consisting of hydrogen, halo, nitrile (—CN), nitro (—NO$_2$), sulfonyl (—SO$_2$R), sulfoxide (SOR), sulfonamide (—SO$_2$NR), sulfonate (—SO$_3$R), trifluoromethyl (—CF$_3$), ester (CO—OR), amide (—CO—NHR or —CO—NRR'), straight-chain or branched (substituted or unsubstituted) $C_1$–$C_{12}$ alkoxy, straight-chain or branched (substituted or unsubstituted) $C_1$–$C_{12}$ alkyl, aromatic or non-aromatic (substituted or unsubstituted) heterocyclic, substituted or unsubstituted aryl, mon- or di-(substituted or unsubstituted) aryl-amine, and (substituted or unsubstituted)alkyl-(substituted or unsubstituted)aryl-amine. In the forgoing substituent group, R and R' are, for example, substituted or unsubstituted $C_1$–$C_{60}$ alkyl, substituted or unsubstituted aryl, substituted or unsubstituted 5–7 membered heterocyclic. The substituted $C_1$–$C_{60}$ alkyl, aryl and heterocyclic are optionally substituted with one or more of amine, amide, ether and ester groups. Alternatively, R1–R6 are independently selected from substituted or unsubstituted electron withdrawing groups, which are well understood by those of ordinary skill in the art. The aryl group includes phenyl, biphenyl, terphenyl, bezyl, naphtyl, antracenyl, tetracenyl, pentacenyl, perylenyl and coronenyl, which are singly or multiply substituted or unsubstituted.

Non-limiting examples of the Formula I compounds are shown below as Formula Ia through Formula Ig.

Formula Ia

Formula Ib

Formula Ic

Formula Id

Formula Ie

Formula If

Formula Ig

The present invention will now be explained in more detail.

Figure 1:
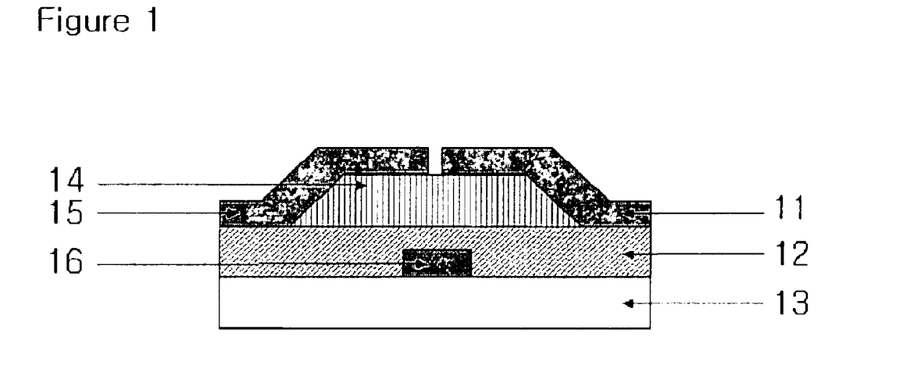
FIG. 1 is a simplified cross-sectional view of an organic transistor.
Figure 2:
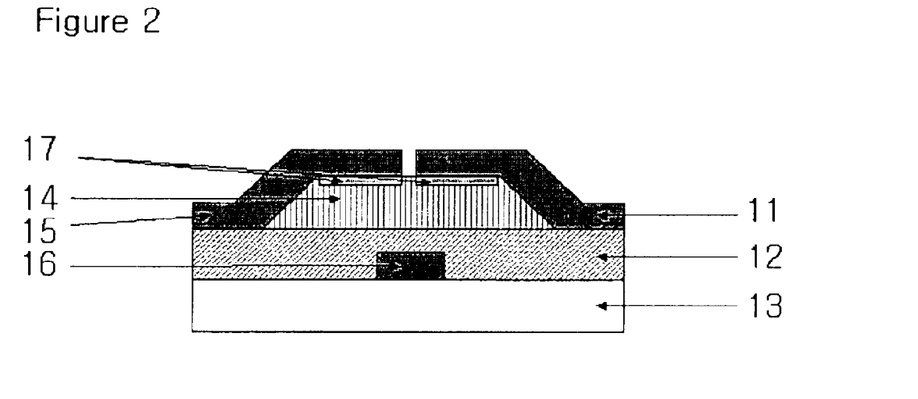
FIGS. 2–4 are simplified cross-sectional views each of an organic transistor having an organic layer according to examples of the present invention.
Figure 3:
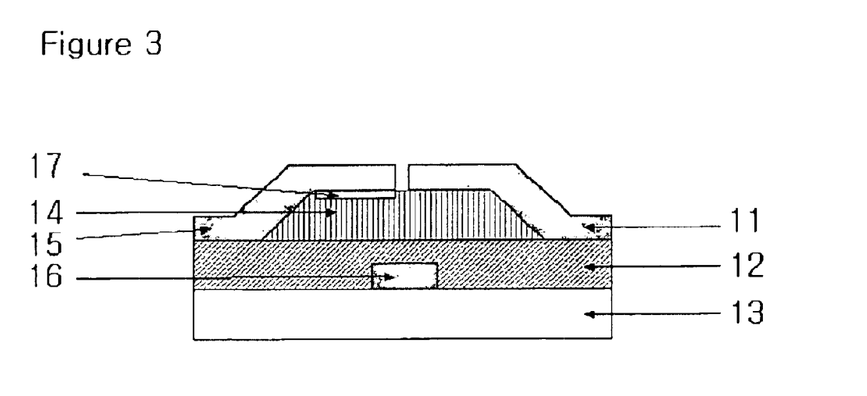
Figure 4:
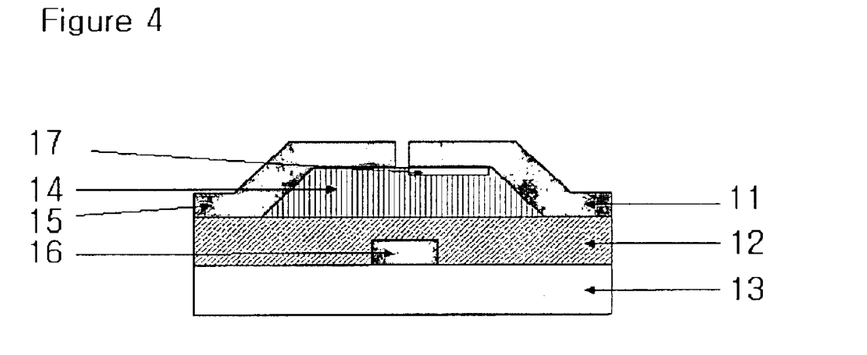

Referring now to FIG. 1, an organic transistor is an electronic device with three terminals called a source electrode 15, a drain electrode 11, and a gate electrode 16. Numerous structures of organic transistors exist. Some examples using the present invention are shown in FIGS. 2–4. An insulating layer 12 is formed above the gate electrode 16, which is patterned onto a substrate 13 as illustrated in FIG. 1. After a semi-conducting (p- or n-type) layer 14 is formed on top of insulating layer 13, the source/drain electrodes are formed on the top of semi-conducting layer 14 and insulating layer 15 as illustrated.

An organic layer 17 comprising at least one compound represented by the Chemical Formula I is inserted between a semi-conducting layer 14 and source/drain electrodes (FIG. 2) or only source electrode 15 (FIG. 3) or only drain electrode 11 (FIG. 4) in accordance with exemplary embodiments. The charge-carrier can be formed in the semi-conducting layer 14 by applying voltage to gate electrode 16. For example, the positive charge-carrier (hole) can be formed in a p-type semi-conducting layer by using negative gate voltage, while the negative charge-carrier (electron) can be formed in an n-type semi-conducting layer by using positive gate voltage. The density of charge-carriers in the semi-conducting layer can be modulated by gate voltage, so that the current-flow between source and drain electrodes can be controlled by the voltage applied to gate electrode.

Further, although not shown in figures, an organic transistor according to another exemplary embodiment may include a gate electrode 16 disposed in a substrate 13, an insulating layer 12 disposed over the gate electrode 16 and the substrate 13, source and drain electrodes 15 and 11 disposed on the insulating layer12, a semi-conducting layer 14 disposed over the insulating layer 12, the source and drain electrodes 15 and 11 and an organic layer 17 inserted between the semi-conducting layer 14 and the source and drain electrodes 15 and 11 or only the source electrode 15 or only the drain electrode 11. Furthermore, an organic transistor according to another exemplary embodiment includes source and drain electrodes 15 and 11 disposed in a substrate 13, a semi-conducting layer 14 disposed over the substrate 13 and the source and drain electrodes 15 and 11, an insulating layer 12 disposed on the semi-conducting layer 14, a gate electrode 16 disposed in the insulating layer 12, and an organic layer 17 inserted between the semi-conducting layer 14 and the source and drain electrodes 15 and 11 or only the source electrode 15 or only the drain electrode 11. Still further, the organic transistor according to another exemplary embodiment, the organic transistor includes a semi-conducting layer 14 disposed in a substrate 13, source and drain electrodes 15 and 11 disposed in the semi-conducting layer 14, an insulating layer 12 disposed on the semi-conducting layer 14 and the source and drain electrodes 15 and 11, a gate electrode 16 disposed in the insulating layer 12 and an organic layer 17 inserted between the semi-conducting layer 14 and the source and drain electrodes 15 and 11 or only the source electrode 15 or only the drain electrode 11.

Each component used in organic transistors and the effect of the present invention will now be explained in more detail.

Substrate

Glass, semiconductor wafers, metal oxide, ceramic materials, and plastics satisfying thermodynamic and mechanical requirements for organic transistors can be used as substrate 13. For example, glass or plastic is used for substrate 13.

Gate Electrode

Conductive materials can be used for the gate electrode 16, including, but not limited to, carbon, aluminum, vanadium, chromium, copper, zinc, silver, gold, magnesium, calcium, sodium, potassium, titanium, indium, yttrium, lithium, gadolinium, aluminum, silver, tin, lead, similar metals, and alloys of the foregoing metals; p- or n-doped silicon; zinc oxide, indium oxide, indium tin oxide (ITO), indium zinc oxide and similar tin oxide or tin oxide indium-based complex compounds; mixtures of oxides and metals, such as ZnO:Al, $SnO_2$:Sb; and conductive polymers, such as poly[3-methylthiophene), poly[3,4-(ethylene-1,2-dioxy)thiophene], polypyrrole and polyaniline.

Insulating Layer

Insulator materials can be used in the insulating layer 12, including, but not limited to, silicon oxide, silcon nitride;

and a plastic insulator such as polyimide, poly(2-vinylpyridine), poly(4-vinylphenol), polymethyl methacrylate, for example.

Semi-Conducting Layer

There are two types of molecules, which can be used in semi-conducting layer 14; p- and n-type organic semi-conducting materials. Holes are the charge-carrier in the case of p-type semi-conducting materials while electrons are the charge-carrier in the case of n-type semi-conducting materials. P-type organic semi-conducting materials include, but are not limited to, pentacene, antradithiophene, benzodithiophene, thiophene oligomers, polythiophenes, mixed-subunit thiophene oligomers, oxy-funcionalized thiophene oligomers (H. E. Katz et al., Acc. Chem. Res. 34, 359 (2001)). N-type organic semi-conducting materials include fluorinated metallophtahlocyanines (Z. Bao, J. Am. Chem. Soc. 120, 207 (1998)), perfluoroarene-modified polythiophene (A. Facchetti, Angew. Chem. Int. Ed. 42, 3900 (2003)), for example.

Organic Layer

An organic layer 17 comprises at least one compound represented by the Chemical Formula I. The introduction of the organic layer 17 helps the establishment of ohmic contact between a semi-conducting layer 14 and source/drain electrodes 15 and 11 or only source electrode 15 or only drain electrode 11. Therefore, the threshold voltage and the charge-carrier mobility in an organic transistor can improve with the organic layer 17 comprising at least one compound by the Chemical Formula I described above.

Source/Drain Electrodes

Conductive materials can be used for the source/drain electrodes, including, but not limited to, carbon, aluminum, vanadium, chromium, copper, zinc, silver, gold, magnesium, calcium, sodium, potassium, titanium, indium, yttrium, lithium, gadolinium, silver, tin, lead, neodymium, platinum, similar metals, and alloys of the foregoing metals; p- or n-doped silicon; zinc oxide, indium oxide, indium tin oxide (ITO), indium zinc oxide and similar tin oxide or tin oxide indium-based complex compounds; mixtures of oxides and metals, such as ZnO:Al, SnO$_2$:Sb; and conductive polymers, such as poly(3-methylthiophene), poly[3,4-(ethylene-1,2-dioxy) thiophene], polypyrrole and polyaniline.

In addition, materials for source/drain electrodes have a suitable work function to reduce the charge-carrier injection barrier and form an ohmic contact with organic layers. When p-type materials are used in semi-conducting layer 14, the work functions of source/drain electrode materials match or are close to a highest occupied molecular orbital (HOMO) level of p-type organic materials. Therefore, metals with a large work function are preferred for the source/drain electrodes, including palladium, platinum, and gold. When n-type materials are used in semi-conducting layer 14, the work functions of source/drain electrode materials match or are close to a lowest unoccupied molecular orbital (LUMO) level of p-type organic materials. Therefore, metals with a small work function are preferred for the source/drain electrodes, including aluminum.

Figure 6:
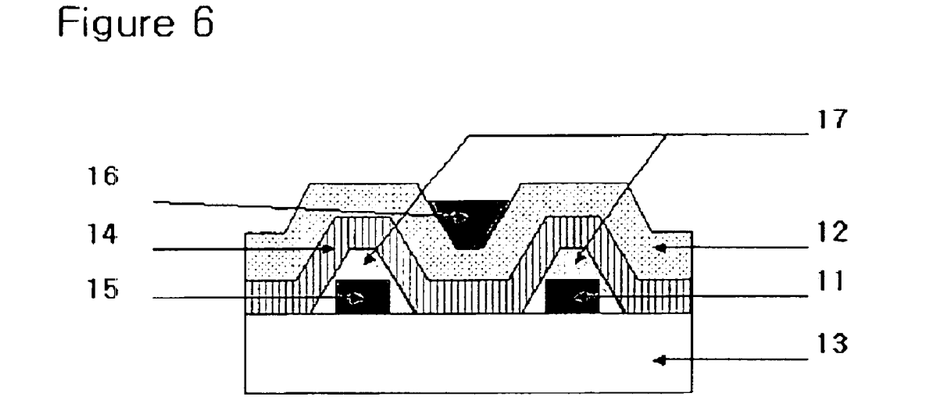
FIG. 6 shows a simplified cross-sectional view of an organic transistor according to examples of the present invention.

However, according to the present invention, the performance of an organic transistor with the organic layer 17 showed weak dependence on source/drain electrode materials. It allows us to fabricate organic transistors in various ways, including screen-printing, reel-to-reel process (J. A. Rogers et al., Adv. Mater. 11, 741 (1999)), micro-contact printing and so on. Therefore, there are a variety of electrode materials that can be used for the source/drain electrode without deteriorating the performance of the organic transistor with the organic layer 17. For example, the use of the organic layer represented by the Chemical Formula 1 allows the use of aluminum as source/drain electrodes in the configuration of FIG. 6. As shown in FIG. 6, aluminum can be easily patterned to make the array of source and drain electrodes 15 and 11 by using photolithography techniques and etching methods. Further, silver paste, which is one of screen printable conductive inks and can be patterned by screen-printing method (C. Gray et al., Proceedings of SPIE-The International Soc. Opt. Eng. 4466, 89 (2001)), can be used as source/drain electrodes

EXAMPLE 1

Figure 5:
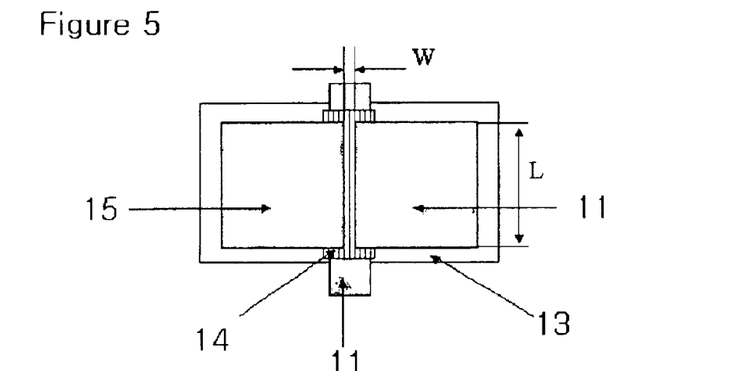
FIG. 5 is a simplified top view of an organic transistor having an organic layer as in FIG. 2 according to examples of the present invention.

The field-effect transistors were fabricated in a staggered-inverted structure as shown in FIGS. 2 and 5. An ITO glass was used as the substrate 13. An ITO electrode is patterned as a gate electrode 16. The gate dielectric or insulator layer 12 was prepared by spin-coating the poly-4-vinylphenol (PVP) solution (15 wt % in propylene glycol monomethyl ether acetate (PGMEA)) at 2000 rpm and curing at 200° C. for 2 hours. The thickness of the PVP gate insulator was 922 nm. The semi-conducting layer 14 is formed on top of the PVP gate dielectric layer 12. Pentacene is used as a p-type semi-conducting materials. Pentacene semi-conducting layer 14 was deposited with a rate of 0.5 Å/s under the base pressure of 1×10$^{-6}$ Torr. The thickness of pentacene layer is 100 nm. The organic layer 17 and gold (Au) source/drain electrodes 15 and 11, respectively, were deposited on top of the pentacene film through a shadow mask as shown in FIG. 2. The organic layer 17 was deposited on top of the pentacene film prior to the deposition of Au electrodes 15, 11 as shown in FIG. 2. The compound represented by Formula Ia was used for the organic layer 17. The organic layer 17 was deposited with a rate of 0.5 Å/s under the base pressure of 1×10$^{-6}$ Torr and the thickness of the organic layer 17 is 40 nm. As shown in FIG. 5, a channel length (L) and width (W) of the organic FET have a profound effect on the performance of the organic transistor. The channel length and width of the organic FET in FIG. 5 are 2 mm and 50 μm, respectively, in accordance with an exemplary embodiment.

Figure 7:
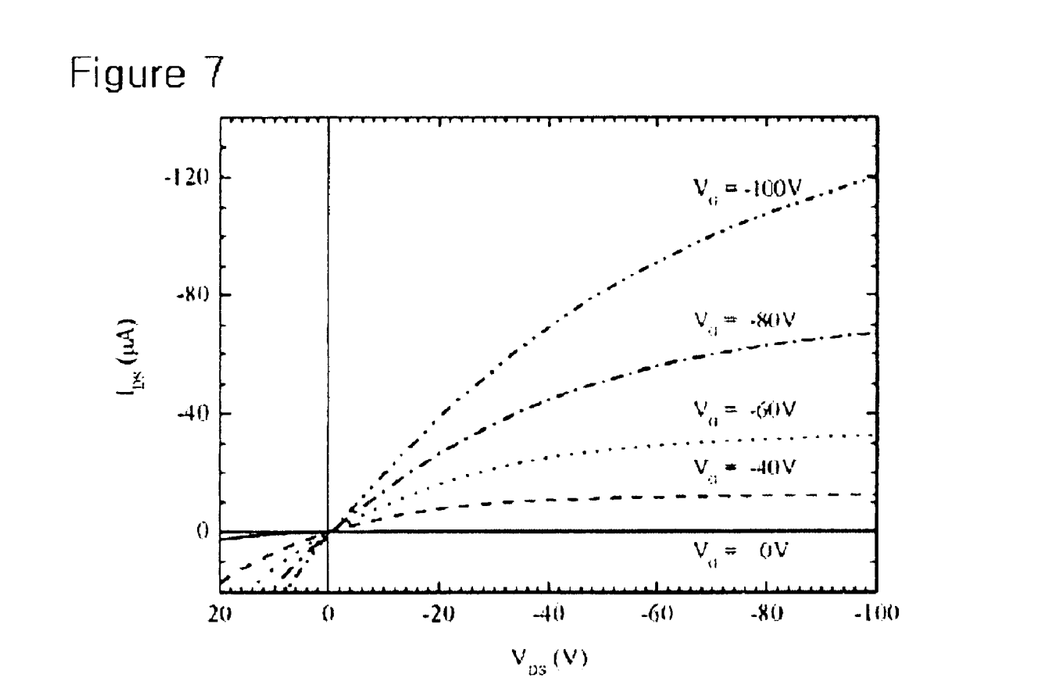
FIGS. 7–10 are graphs of drain-source current ($I_{DS}$) versus drain-source voltage ($V_{DS}$) characteristics for several gate voltages ($V_G$).
Figure 11:
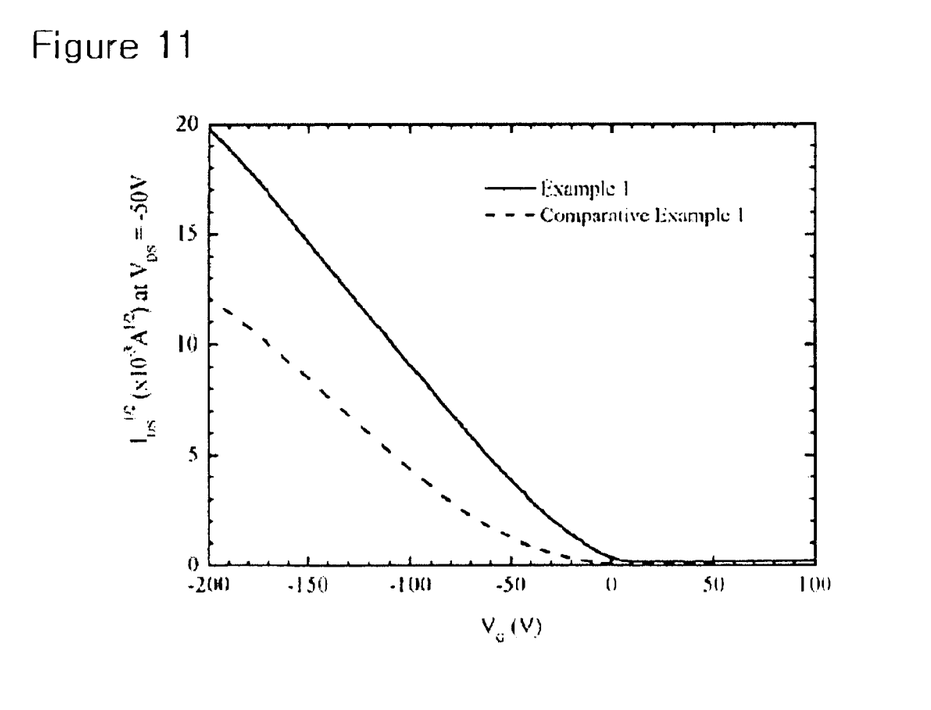
FIGS. 11 and 12 are graphs of the $(I_{DS})^{1/2}$ versus $V_G$ characteristics for pentacene transistors.
Figure 12:
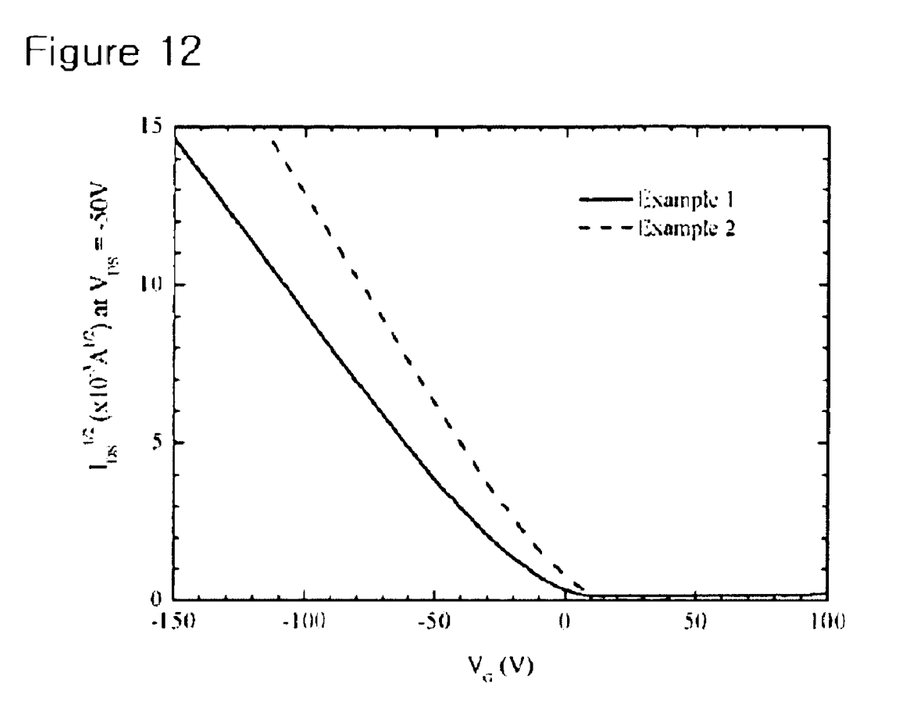

A graph illustrating the drain-source current ($I_{DS}$) versus drain-source voltage ($V_{DS}$) characteristics for several gate voltages ($V_G$) is shown in FIG. 7. The $(I_{DS})^{1/2}$ versus $V_G$ characteristics for pentacene transistors ($V_{DS}$=−50V) is shown in FIG. 11 and 12. In the saturation regime of the drain-source current, the field-effect mobility is calculated as $\mu_{FET}$=0.16 cm$^2$/Vs.

EXAMPLE 2

The device was fabricated the same way as described in Example 1 except for replacing Au with Al as source/drain electrodes.

Figure 8:
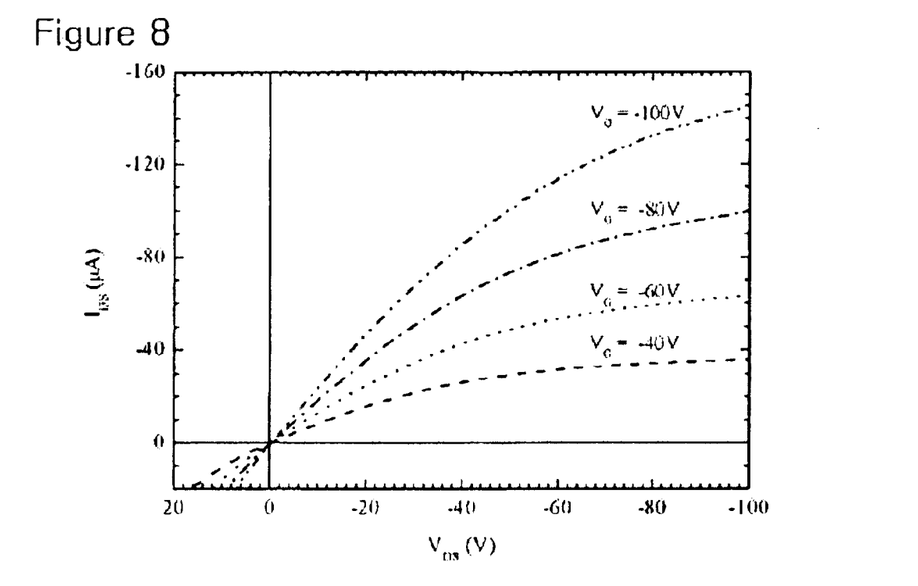

A graph illustrating the drain-source current ($I_{DS}$) versus drain-source voltage ($V_{DS}$) characteristics for several gate voltages ($V_G$) is shown in FIG. 8. A graph illustrating the $(I_{DS})^{1/2}$ versus $V_G$ characteristics for pentacene transistors ($V_{DS}$=−50V) is shown in FIG. 12. In the saturation regime of the drain-source current, the field-effect mobility is calculated as $\mu_{FET}$=0.18 cm$^2$/Vs.

COMPARATIVE EXAMPLE 1

The device was fabricated the same way as described in Example 1 except for the absence of the organic layer 17 as being shown absent in FIG. 1.

Figure 9:
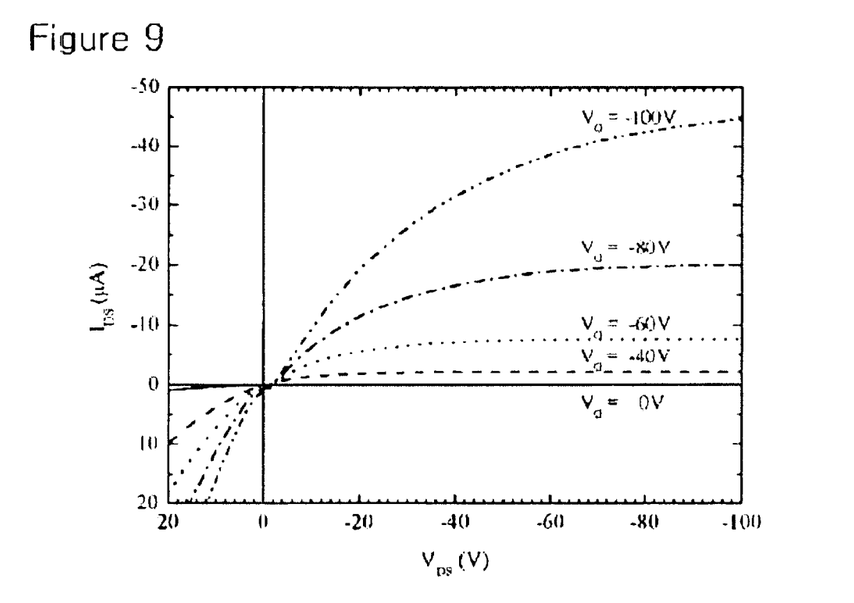

A graph illustrating the drain-source current ($I_{DS}$) versus drain-source voltage ($V_{DS}$) characteristics for several gate voltages ($V_G$) is shown in FIG. 9. A graph illustrating the $(I_{DS})^{1/2}$ versus $V_G$ characteristics for pentacene transistors ($V_{DS}$=−50V) is shown in FIG. 11. In the saturation regime of the drain-source current, the field-effect mobility is calculated as $\mu_{FET}$=0.07 cm$^2$/Vs.

COMPARATIVE EXAMPLE 2

The device was fabricated the same way as described in Comparative Example 1 except for replacing Au with Al as source/drain electrodes.

Figure 10:
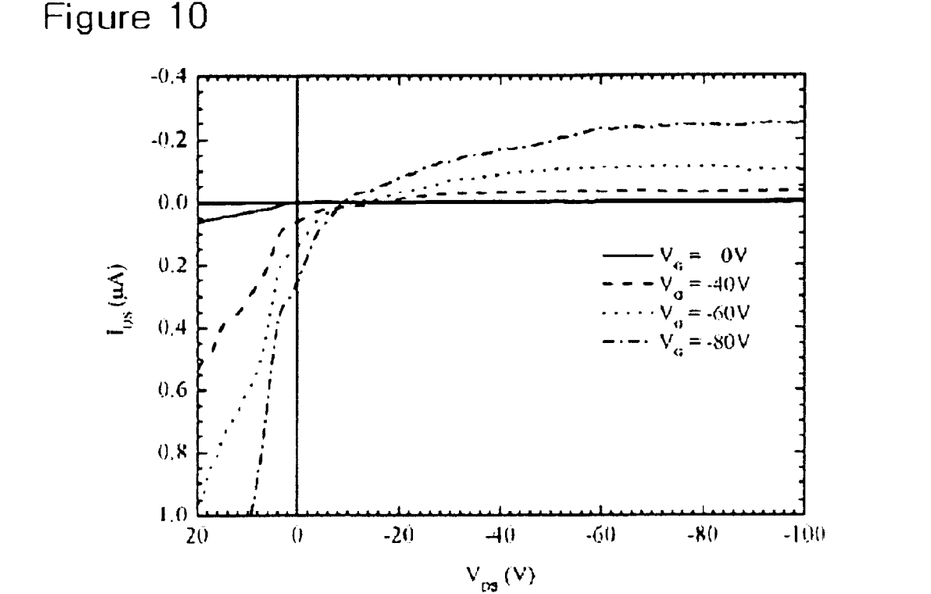

A graph illustrating the drain-source current ($I_{DS}$) versus drain-source voltage ($V_{DS}$) characteristics for several gate voltages ($V_G$) is shown in FIG. 10. It will be recognized that the device shows very poor and unstable transistor characteristics.

Under the same gate biases, the source-drain current has a higher value for the transistor with the organic layer 17 between pentacene and Au electrode (FIG. 7) than that for the transistor without the organic layer 17 (FIG. 9). A graph illustrating the $(I_{DS})^{1/2}$ versus $V_G$ characteristics for pentacene transistors with and without the organic layer is shown in FIG. 11. FIG. 11 clearly shows that the usage of the organic layer 17 in an organic transistor improves the performance of the device by more than a factor of 2, as seen when $V_G$ is between about 0V and about −140V.

The organic transistors with the organic layer 17 also showed a similar performance using Au or Al for the source/drain electrode materials (See FIGS. 7, 8, and 12). FIGS. 11 and 12 clearly demonstrate the benefit of an organic layer inserted between a semi-conducting layer and source and/or drain electrodes for fabricating organic transistor arrays using a lithography technique.

What is claimed is:

1. An organic transistor, comprising:
   an organic layer inserted between a p-type organic semi-conducting layer and a source or drain electrode,
   wherein the organic layer includes at least one compound represented by Chemical Formula I Formula I 2. The organic transistor of claim 1, wherein the organic layer is further inserted between the semi-conducting layer and the source and drain electrodes.

3. The organic transistor of claim 1, further comprising:
   a substrate;
   a gate electrode disposed in the substrate;
   an insulating layer disposed over the gate electrode and the substrate;
   the semi-conducting layer disposed on the insulating layer; and
   the source and drain electrodes disposed over the semi-conducting layer and the insulating layer.

4. The organic transistor of claim 1, further comprising:
   a substrate;
   a gate electrode disposed in the substrate;
   an insulating layer disposed over the gate electrode and the substrate;
   the source and drain electrodes disposed on the insulating layer; and
   the semi-conducting layer disposed over the insulating layer and the source and drain electrodes.

5. The organic transistor of claim 1, further comprising:
   a substrate;
   the source and drain electrodes disposed on the substrate;
   the semi-conducting layer disposed over the substrate and the source and drain electrodes;
   an insulating layer disposed on the semi-conducting layer; and
   a gate electrode disposed in the insulating layer.

6. The organic transistor of claim 1, further comprising:
   a substrate;
   the semi-conducting layer disposed in the substrate;
   the source and drain electrodes disposed in the semi-conducting layer;
   an insulating layer disposed on the semi-conducting layer and the source and drain electrodes; and
   a gate electrode disposed in the insulating layer.

7. The organic transistor of claim 1, wherein the source or drain electrode include aluminum, silver, gold, neodymium, palladium, platinum, gold, or alloys of the foregoing metals.

8. The organic transistor of claim 1, wherein the source or drain electrode include composite materials including aluminum or silver.

9. The organic transistor of claim 1, wherein the chemical compound I includes one of the following compounds Ia to Ig

Formula Ia

Formula Ib

10. A method for manufacturing an organic transistor, comprising:

inserting an organic layer between a p-type organic semi-conducting layer and a source or drain electrode to improve electric contact between the semi-conducting layer and the source or drain electrode, wherein the organic layer includes at least one compound represented by Chemical Formula I Formula I 11. The method of claim 10, further comprising inserting the organic layer between the semi-conducing layer and the source and drain electrodes.

12. The method of claim 10, further comprising:

forming a gate electrode in a substrate;

forming an insulating layer over the gate electrode and the substrate;

forming the semi-conducting layer on the insulating layer; and forming the source and drain electrodes over the semi-conducting layer and the insulating layer.

13. The method of claim 10, further comprising:

forming a gate electrode in a substrate;

forming an insulating layer over the gate electrode and the substrate;

forming the source and drain electrodes on the insulating layer; and forming the semi-conducting layer over the insulating layer and the source and drain electrodes.

14. The method of claim 10, further comprising:

forming the source and drain electrodes on a substrate;

forming the semi-conducting layer over the substrate and the source and drain electrodes;

forming an insulating layer on the semi-conducting layer; and forming a gate electrode in the insulating layer.

15. The method of claim 10, further comprising:

forming the semi-conducting layer in a substrate;

forming the source and drain electrodes in the semi-conducting layer;

forming an insulating layer on the semi-conducting layer and the source and drain electrodes; and forming a gate electrode in the insulating layer.

16. The method of claim 10, wherein the chemical compound I includes one of the following compounds Ia to Ig

Formula Ia

Formula Ib

Formula Ic

Formula Id

Formula Ie

Formula If

-continued

Formula Ig

17. The method of claim 10, further comprising forming the source and drain electrodes as one of aluminum, silver, gold, neodymium, palladium, platinum, gold, and alloys of the foregoing metals.

18. The method of claim 10, further comprising forming the source and drain electrodes with composite materials including aluminum or silver.

19. An organic transistor, comprising:
an organic layer disposed on a p-type organic semiconducting layer, the organic layer including at least one compound represented by Chemical Formula I Formula I

* * * * *